US008934981B2

(12) United States Patent
De Ridder (10) Patent No.: US 8,934,981 B2
(45) Date of Patent: Jan. 13, 2015

(54) SPINAL CORD STIMULATION TO TREAT PAIN (76) Inventor: Dirk De Ridder, Zelzate (BE)

(*) Notice: Subject to any disclaimer, the term of this patent is extended or adjusted under 35 U.S.C. 154(b) by 0 days.

(21) Appl. No.: 13/550,196

(22) Filed: Jul. 16, 2012

(65) Prior Publication Data
US 2012/0283797 A1 Nov. 8, 2012

Related U.S. Application Data (63) Continuation of application No. 12/047,104, filed on Mar. 12, 2008, now Pat. No. 8,224,453.

(60) Provisional application No. 60/895,061, filed on Mar. 15, 2007.

(51) Int. Cl.
*A61N 1/34* (2006.01)
*A61N 1/36* (2006.01)
*A61N 1/05* (2006.01)
*A61N 1/372* (2006.01)

(52) U.S. Cl.
CPC ......... *A61N 1/36071* (2013.01); *A61N 1/37247* (2013.01)
USPC ............................... 607/46; 607/45; 607/117

(58) Field of Classification Search
USPC ..................... 607/2, 3, 30, 31, 45, 46, 117
See application file for complete search history.

(56) References Cited

U.S. PATENT DOCUMENTS

| 4,541,432 | A | 9/1985 | Molina-Negro et al. |
| 5,938,690 | A | 8/1999 | Law et al. |
| 6,295,472 | B1 | 9/2001 | Rubinstein et al. |
| 6,466,822 | B1 | 10/2002 | Pless |
| 6,609,031 | B1 | 8/2003 | Law et al. |
| 6,690,974 | B2 | 2/2004 | Archer et al. |
| 6,748,276 | B1 | 6/2004 | Daignault, Jr. et al. |
| 6,944,501 | B1 | 9/2005 | Pless |
| 7,054,686 | B2 | 5/2006 | MacDonald |
| 7,295,876 | B1* | 11/2007 | Erickson ......................... 607/46 |
| 7,463,927 | B1* | 12/2008 | Chaouat ........................ 607/46 |
| 8,224,453 | B2 | 7/2012 | DeRidder |
| 2002/0091423 | A1 | 7/2002 | Rubinstein et al. |
| 2003/0120323 | A1* | 6/2003 | Meadows et al. ............... 607/46 |
| 2003/0135248 | A1 | 7/2003 | Stypulkowski |
| 2004/0133248 | A1 | 7/2004 | Frei et al. |

(Continued)

OTHER PUBLICATIONS

Alo, et al., "Computer Assisted and Patient Interactive Programming of Dual Octrode Spinal Cord Stimulation in the Treatment of Chronic Pain", Neuromodulation, vol. 1, No. 1, pp. 30-45, 1998, Blackwell Science Inc.

(Continued)

*Primary Examiner* — Christopher D Koharski
*Assistant Examiner* — Pamela M Bays (57) ABSTRACT

A system and method for treating pain without paresthesia by spinal cord stimulation. In one embodiment, a method comprises storing one or more operating parameters for a high frequency stimulus having a plurality of pulses, wherein the high frequency stimulus comprises at least respective pairs of pulses that have an inter-pulse separation within a range of 0.1 milliseconds to 10 milliseconds; and applying generated electrical pulses of the high frequency stimulus to the patient through a set of one or more electrodes of an electrical lead implanted within epidural space of the patient to treat the chronic pain of the patient without causing paresthesia in the patient.

17 Claims, 7 Drawing Sheets

(56) References Cited

U.S. PATENT DOCUMENTS

| | | | |
|---|---|---|---|
| 2004/0210271 | A1 | 10/2004 | Campen et al. |
| 2005/0070971 | A1 | 3/2005 | Fowler et al. |
| 2005/0119713 | A1* | 6/2005 | Whitehurst et al. ............ 607/46 |
| 2005/0246006 | A1* | 11/2005 | Daniels ........................ 607/117 |
| 2006/0015153 | A1 | 1/2006 | Gliner et al. |
| 2006/0030899 | A1* | 2/2006 | O'Keeffe et al. ............... 607/46 |
| 2006/0095088 | A1 | 5/2006 | DeRidder |
| 2006/0190056 | A1 | 8/2006 | Fowler et al. |
| 2010/0274312 | A1* | 10/2010 | Alataris et al. ................. 607/46 |

OTHER PUBLICATIONS

Beurrier, et al., "Subthalamic nucleus neurons switch from single-spike activity to burst-firing mode," J. Neurosci., 19 (2): 599-609, 1999.

DeRidder, Dirk, et al., "Activation of cortical and subcortical auditory structures at 3T by means of a functional magnetic resonance imaging paradigm suitable for clinical use," Invest Radiol. 41(2): 87-96, Feb. 2006.

DeRidder, Dirk, et al., "Do tonic and burst TMS modulate the lemniscal and extralemniscal system differentially?" Int. J. Med. Sci., 4(5):242-246, 2007.

DeRidder, Dirk, et al., "Theta, alpha and beta burst transcranial magnetic stimulation: brain modulation in tinnitus," Int. J. Med. Sci., 4(5):237-241, 2007.

DeRidder, Dirk, et al., "Transcranial magnetic stimulation for tinnitus influence of tinnitus duration on stimulation parameter choice and maximal tinnitus suppression," Otol. Neurotol. 26(4): 616-9, Jul. 2005.

DeRidder, Dirk, et al.; Magnetic and electrical stimulation of the auditory cortex for intractable tinnitus: J. Neurosurg, 100:560-564, 2004.

Flor, "Cortical reorganisation and chronic pain: implications for rehabilitation," J. Rehabil. Med., (41 Suppl): 66-72, 2003.

He, et al., "Differential distribution of burst and single-spike responses in auditory thalamus," J. Neurophysiol., 88(4): 2152-6, 2002.

Huang, et al., "Theta burst stimulation of the human motor cortex," Neuron, 45(2): 201-6, 2005.

Interpulse interval definition found at "The Free Dictionary" by Farlex; http://medical-dictionary.thefreedictionary.com/interpulse+interval.

Johnson, "Discharge frequencies and intervals between pulses: arethey always the same?" Brain Research 666 (1994) 125-127.

Joliot, et al., "Human oscillatory brain activity near 40 Hz coexists with cognitive temporal binding," Proc. Natl. Acad. Sci. USA, 91(24): 11748-51, 1994.

Kaas, et al., "The reorganization of somatosensory cortex following peripheral nerve damage in adult and developing mammals," Annu. Rev. Neurosci., 6: 325-56, 1983.

Kepecs, et al., "Bursting neurons signal input slope," J. Neurosci., 22(20): 9053-62, 2002.

Lenz, et al., "Characteristics of the bursting pattern of action potentials that occurs in the thalamus of patients with central pain," Brain Res., 496(1-2): 357-360, 1989.

Lisman, John E.; Bursts as a unit of neural information: making unreliable synapses reliable; Trends Neurosci., 20 (1):38-43, 1997.

Londero, et al., "Repetitive transcranial magnetic stimulation (rTMS): a new therapeutic approach in subjective tinnitus?" Neurophysiol. Clin., 36(3): 145-55. Epub Aug. 22, 2006 May-Jun. 2006.

Schwindt, et al., "Mechanisms underlying burst and regular spiking evoked by dendritic depolarization in layer 5 cortical pyramidal neurons," Neurophysiol., 81(3): 1341-54, 1999.

Tsubokawa, et al., "Chronic motor cortex stimulation for the treatment of central pain," Acta Neurochir. Suppl., 52: 137-139, 1991.

Tsubokawa, et al., "Treatment of thalamic pain by chronic motor cortex stimulation," Pacing Clin. Electrophysiol., 14(1): 131-134, 1991.

Urbain, et al., "The switch of subthalamic neurons from an irregular to a bursting pattern does not solely depend on their GABAergic inputs in the anesthetic-free rat," J. Neurosci., 22(19): 8665-8675, 2002.

Buyten et al., High-Frequency Spinal Cord Stimulation for the Treatment of Chronic Back Pain Patients: Results of a Prospective . . . Neuromodulation 2013; 16: 59-66 (2012).

Wolter et al., Effects of sub-perception threshold spinal cord stimulation in neuropathic pain: A randomized controlled double-blind crossover study, Eur J Pain 16 (2012).

* cited by examiner

SPINAL CORD STIMULATION TO TREAT PAIN

CROSS-REFERENCE TO RELATED APPLICATIONS

This application is a continuation of U.S. application Ser. No. 12/047,104, filed Mar. 12, 2008, now U.S. Pat. No. 8,224,453, which claims the benefit of U.S. Provisional Application No. 60/895,061, filed Mar. 15, 2007, the disclosures of which are incorporated herein by reference.

TECHNICAL FIELD

The present application relates the fields of medicine, more specifically neuromodulation. In certain aspects, the present application relates to neuromodulation for medical treatment, and more particularly to stimulating neuronal tissue in the spinal cord for treating pain without paresthesia.

BACKGROUND

Spinal cord stimulation (SCS) has been used as a treatment for chronic painful conditions for approximately thirty years. Commonly, SCS is used to alleviate pain after failed surgery, pain due to neuropathies, or pain due to inadequate blood flow. SCS originated shortly after the publication of Melzack and Wall's "Gate Control Theory." The theory essentially states that mutual inhibitory connections exist between slow conducting nociceptive C-fiber sensory neurons and fast conducting non-nociceptive $A\beta$ fiber sensory neurons. Whether or not this mutual inhibition is direct and/or indirect via inhibitory interneurons is not completely understood, but it is known that this inhibitory effect can be seen at the level of the second order dorsal horn neurons that project both nociceptive and non-nociceptive sensory information to the brain. Thus, the therapeutic effect of spinal cord stimulation may act according to the principals of Gate Control Theory or it may be efficacious due to as yet poorly understood mechanisms (e.g., inhibitory interneuron activation, pain perception modulation in the brain). Regardless of the specific mechanism, those skilled in the art have stimulated non-nociceptive fibers as a therapy to alleviate pain symptoms in cases of chronic pain.

In practical application, electrodes are implanted within the epidural space for delivery of electrical stimulation. The electrodes are coupled to a pulse generator which generates high frequency stimulation pulses. Specifically, conventional spinal cord stimulation applies stimulation pulses to neural tissue of the dorsal column in a regular pattern with each pulse being separated by a fixed inter-pulse interval that defines the stimulation frequency. It is believed that high frequency tonic stimulation acts as a "digital lesion" which prevents communication of pain signals to the thalamus of the patient. Specifically, high frequency stimulation has been observed to prevent the perception of certain types of pain by patients. Instead of perceiving pain, the high frequency electrical stimulation causes other sensation signals to reach the thalamus whereby the patient experiences a tingling sensation known medically as paresthesia. Although the paresthesia can be uncomfortable or even painful in patients, the paresthesia is usually substantially more tolerable than the pain previously experienced by the patients and, hence, is considered an acceptable negative side-effect.

BRIEF SUMMARY

The claimed material comprises a therapeutic system for treating pain having a surgically implanted device in communication with a spinal cord treatment site. The device can include a distal probe, such as, for example, an electrode assembly or electrical stimulation lead. The proximal end of the probe may be coupled to an electrical signal source, which, in turn, may be operated to stimulate the predetermined dorsal column treatment site. Later embodiments stimulate the dorsal column or posterior funiculus, which is located between the posterior median septum and the posterior horn in the spinal column.

The foregoing has outlined rather broadly the features and technical advantages of the claimed material in order that the detailed description that follows may be better understood. Additional features and advantages will be described hereinafter which form the subject of the claims. It should be appreciated that the conception and specific embodiment disclosed may be readily utilized as a basis for modifying or designing other structures for carrying out the same purposes. It should also be realized that such equivalent constructions do not depart from the material set forth in the appended claims. The novel features which are believed to be characteristic of the claimed material, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the claimed material.

BRIEF DESCRIPTION OF THE DRAWING

For a more complete understanding of the claimed material, reference is now made to the following descriptions taken in conjunction with the accompanying drawing, in which:

FIGS. 3A-3B illustrates pain scores.

DETAILED DESCRIPTION

I. Definitions

Unless defined otherwise, technical and scientific terms used herein have the same meaning as commonly understood by one of ordinary skill in the art to which the claimed material belongs. The following terms are defined below.

As used herein, the use of the word "a" or "an" when used in conjunction with the term "comprising" in the claims and/or the specification may mean "one", but it is also consistent with the meaning of "one or more," "at least one", and "one or more than one". Still further, the terms "having", "including", "containing" and "comprising" are interchangeable and one of skill in the art is cognizant that these terms are open-ended terms.

As used herein, the term "in communication" refers to the stimulation lead being adjacent, in the general vicinity, in close proximity, or directly next to or directly on the predetermined stimulation site. Thus, one of skill in the art understands that the lead is "in communication" with the predetermined site if the stimulation results in a modulation of neuronal activity. The predetermined site may be selected from the group consisting of the spinal cord, and the dorsal column of the spinal cord which may include the spinal cord area corresponding to cervical vertebral segments C1 to C8, thoracic vertebral segments T1 to T12, or lumbar vertebral segments L1 and L2. One of ordinary skill in the art will understand that the spinal cord normally terminates at the second lumbar vertebrae L2. However, in certain subjects the spinal cord may terminate before or after the L2 vertebrae segment, and the claimed material is intended for use along the entire length of the spinal cord regardless of length.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T11 nerve root leaves the spinal cord myelum at an area located behind vertebral body T8-T9 but leaves the bony spine between T11 and T12.

As used herein, the use of the term "dorsal column" refers to conducting pathways in the spinal cord that are located in the dorsal portion of the spinal cord between the posterior horns, and which comprises afferent somatosensory neurons. The dorsal column is also known as the posterior funiculus.

As used herein, the use of the words "epidural space" or "spinal epidural space" is known to one with skill in the art, and refers to an area in the interval between the dural sheath and the wall of the spinal canal.

As used herein, the term "neuronal" refers to a neuron which is a morphologic and functional unit of the brain, spinal column, and peripheral nerves.

As used herein, the term "somatosensory system" refers to the peripheral nervous system division comprising primarily afferent somatic sensory neurons and afferent visceral sensory neurons that receive sensory information from skin and deep tissue, including the 12 cranial and 21 spinal nerves.

As used herein, the term "stimulate" or "stimulation" refers to electrical, chemical, heat, and/or magnetic stimulation that modulates the predetermined sites in the nervous system.

As used herein, the term "treating" and "treatment" refers to modulating certain areas of the spinal cord so that the subject has an improvement in the disease, for example, improvements in pain without paresthesia. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

As used herein, the terms "spike", "action potential", and "pulse", all refer to a rapid rise and fall of voltage in a specified region of space. One skilled in the art realizes that the term action potential generally refers to a spike or pulse that is produced by a neuron. One skilled in the art also recognizes that the term action potential can also be expanded to include the spiking of cells in other excitable tissues. The terms spike and pulse may refer to action potentials produced by neurons and other excitable cells and may also refer to artificial stimulations that mimic the features of action potentials in cells or groups of cells. The terms "inter-spike interval" or "inter-pulse interval" refer to the period of time between two action potentials, spikes, or pulses. However, one of skill in the art also realizes that naturally occurring spikes do not necessarily occur at a fixed rate; this rate can be variable. In such cases an average inter-spike interval may be used to define the average period of time between consecutive action potentials, spikes, or pulses in a series.

As used herein, the term "burst" refers to a rapid succession of two or more neuronal action potentials or external stimuli in the approximate frequency range of 50-1000 Hz (Beurrier et al., 1999) that, possibly, occurs during a 'plateau' or 'active phase', followed by a period of relative quiescence called the 'silent phase' (Nunemaker, Cellscience Reviews Vol 2 No. 1, 2005.). A burst stimulation may occur from a plateau or elevated pulse amplitude applied by the pulse stimulator. Also, a hyper-polarizing or other pre-conditioning pulse may precede the burst. A charge balancing pulse or pulses may be applied within the burst or at the end of the burst. A burst spike may be described as a spike that is preceded or followed by another spike within a short time interval of approximately (0.1-10 msec) (Matveev, 2000). Those skilled in the art recognize that a burst can refer to a plurality of groups of spike pulses. In some embodiments, a burst may be a period in time in which two or more spikes occur relatively rapidly, such that the spikes summate in the dendrites or cell body of a neuron in a non-linear fashion. The period of time between the beginning of a burst and the end of the same said burst is the "intra-burst interval". The period of time between two bursts is the "inter-burst interval". For example, 1 milliseconds to about 5 seconds, more preferably, about 10 milliseconds to about 300 milliseconds. In some embodiments, the burst stimulus may comprise pulse amplitude ramping, for example increasing the amplitude of successive pulses within an individual burst. One skilled in the art is also aware that burst firing can also be referred to as phasic firing, rhythmic firing (Lee 2001), pulse train firing, oscillatory firing and spike train firing, all of these terms used herein are interchangeable. While not being bound by theory, one of skill in the art is also aware that the burst stimulus can also be defined as amplitude modulation (AM) and/or transient frequency modulation (FM) as it relates to the communication fields.

As used herein, the term "tonic" as well as the phrases "tonic firing", "tonic spike", "tonic pulse", or "tonic mode" refers to any process in which the firing pattern can be accurately described as a series of single spikes of a given frequency or with a given inter-spike interval, wherein the inter-spike interval may be fixed or variable.

The term "pain" as used herein refers to an unpleasant sensation. For example, the subject experiences discomfort, distress or suffering. It is known to one skilled in the art that various painful conditions may be classified according to broadly opposing or otherwise useful categories. Examples of opposing categories include; nociceptive pain versus non-nociceptive pain, and acute pain versus chronic pain. Examples of other common categories of pain used by those skilled in the art include neuropathic pain and phantom pain.

The term "nociception" as used herein refers to the transduction of noxious or potentially injurious stimuli into a sensation.

The term "nociceptive pain" as used herein refers to pain caused by activity in primary sensory pain fibers in the peripheral nervous system. Neurons in the peripheral nervous system that typically respond to noxious or painful stimuli are commonly referred to as nociceptors or nociceptive neurons. Yet further, the nociceoptive pathways extend to the somatosensory cortex.

The term "non-nociceptive pain" as used herein refers to pain caused by activity in neurons in the central nervous system. Examples of neurons in the central nervous system that may cause non-nociceptive pain include neurons in the dorsal horn of the spinal cord such as interneurons and projection neurons, or neurons in parts of the brain known to be involved in pain sensation such as the rostral ventromedial medulla (RVM) and the periaqueductal grey (PAG).

The term "acute pain" as used herein refers to pain that is transient in nature or lasting less than 1 month. Acute pain is typically associated with an immediate injurious process such as soft tissue damage, infection, or inflammation, and serves the purpose of notifying the animal of the injurious condition, thus allowing for treatment and prevention of further injury.

The term "chronic pain" as used herein refers to pain that lasts longer than 1 month or beyond the resolution of an acute tissue injury or is recurring or is associated with tissue injury and/or chronic diseases that are expected to continue or progress. Examples of chronic diseases that are expected to continue or progress may include cancer, arthritis, inflammatory disease, chronic wounds, cardiovascular accidents, spinal cord disorders, central nervous system disorder or recovery from surgery.

The term "neuropathy" as used herein refers to any condition that adversely affects the normal functioning of the nervous system. Neuropathies can originate anywhere in the central or peripheral nervous system, but only in some cases does this produce neuropathic pain.

The term "neuropathic pain" as used herein refers to pain that results from damage to or abnormal function of the nervous system itself. It may exist independently of any form of tissue injury outside of the nervous system. Examples of conditions that may lead to neuropathic pain include disease (e.g., HIV, Herpes, Diabetes, Cancer, autoimmune disorders), acute trauma (surgery, injury, electric shock), and chronic trauma (repetitive motion disorders, chemical toxicity such as alcohol, chemotherapy, or heavy metals).

The term "phantom pain" as used herein refers to a condition whereby the patient senses pain in a part of the body that is either no longer physically present due to amputation, or is known to be completely insensate due to total peripheral nerve destruction.

The term "hyperalgesia" as used herein refers to an increased sensitivity to nociceptive or painful stimuli. The term "allodynia" as used herein describes a condition whereby normally non-noxious stimuli are perceived as painful. Both hyperalgesia and allodynia can be divided into primary and secondary categories or conditions. Primary hyperalgesia/allodynia is an increase in sensitivity to painful and previously non-painful stimuli in a region of the body that has undergone tissue injury. Secondary hyperalgesia/allodynia is an increase in pain sensitivity globally and requires descending input into the periphery from various pain processing centers in the brain.

II. Experimental Section

A. EXAMPLE 1

Introduction

Some neurons fire in packets of action potentials followed by periods of quiescence (bursts) while others, within the same stage of sensory processing, fire in a tonic manner. Burst and tonic firing might be processing information in parallel in certain sensory systems (Ozwald et al., 2004; Chacron et al. 2004). Up to now all neuromodulation devices used in humans were using tonic stimuli, whether magnetic or electrical.

The applicants recently initiated electrical stimulation protocols consisting of intra-burst inter-pulse frequencies of 500 Hz and inter-burst frequencies of 40 Hz, using electrodes implanted on the dorsal column as a treatment for chronic pain.

It was noted that during cervical dorsal column stimulation that no paresthesias were induced at stimulation parameters required for symptom suppression. Using the same stimulation design, the applicants now present the first cases of dorsal column stimulation for pain suppression, wherein pain suppression can be achieved without inducing paresthesias, which was previously a universal side-effect of dorsal column stimulation.

Methods

Patients with intractable pain were implanted with dorsal column electrodes. Before and after treatment patients were asked to measure their pain sensation using the Visual Analog Pain Scale (VAS) in which the pain may be assigned a value between zero and ten with zero representing no pain and ten representing maximum pain experience (Huskisson, 1982). Results of pain suppression with tonic stimulation were compared to burst stimulation, as well as the presence or absence of paresthesia at stimulation parameters used to obtain pain suppression. All patients were implanted extradurally with paddle electrodes (Lamitorode 44, ANS Medical, Plano, Tex., USA), either on the cervical dorsal column at the level of C2 for intractable cervicobrachialgia or on the thoracic dorsal column at the level of T11 for intractable lumboischialgia. Details of the patients are shown below in Table 1.

TABLE 1

| Patient | Inter-Burst Freq (Hz) | Intra-Burst Freq (Hz) | Pulse (#) | Pulse Width (µS) | VAS Pain Scores Before | VAS Pain Scores After |
|---|---|---|---|---|---|---|
| 1 | 40 | 500 | 5 | 1000 | VAS C2 area right: 8 | VAS pain: 0 VAS pressure: 0 (after 10 min)/VAS |
| 2 | 40 | 500 | 5 | 1000 | VAS Left Leg: 8 VAS Right Leg: 8 VAS Back: 8 | All VAS: 0 |

TABLE 1-continued

| Patient | Inter-Burst Freq (Hz) | Intra-Burst Freq (Hz) | Pulse (#) | Pulse Width (µS) | VAS Pain Scores Before | VAS Pain Scores After |
|---|---|---|---|---|---|---|
| 3 | 40 | 500 | 5 | 1000 | VAS Arms: 8 | VAS: 0 Ri Arm, Ri Sch, Le Hnd, + improved mobility hnd, No positional changes, relaxation biceps |
| 4 | 40 | 500 | 5 | 1000 | VAS: Legs 8 VAS: Back 8 | Total system explanted due to infection |
| 5 | 40 | 500 | 5 | 1000 | VAS Left Leg: 9 VAS Right Leg: 9 VAS Back: 9 | With Tonic Stim: VAS Legs: 0 VAS Back 9 Burst Stim: VAS Legs: 0 VAS Back: 0 |
| 6 | 40 | 500 | 5 | 1000 | VAS Back: 6 (range 3-8) VAS left leg: (range 3-8) | Tonic Stim: VAS leg: 0-2 VAS back: 6/5% of 3 mA Burst Stim: VAS back: 2 VAS Leg: 0 |
| 7 | 40 | 500 | 5 | 1000 | VAS R Lower Leg (peroneous area, ankle, foot: 8 | VAS 1-2 |
| 8 | 40 | 500 | 5 | 1000 | Infection | Infection |
| 9 | 40 | 500 | 5 | 1000 | VAS: 8 (Legs, ft and lower left back) | VAS: 0 |
| 10 | 40 | 500 | 5 | 1000 | VAS Legs: 9 VAS Back: 8 | Tonic Stim VAS Legs: 2 VAS Back: 8 Burst Stim: VAS Legs: 0 VAS Back: 0 |

Figure 1:
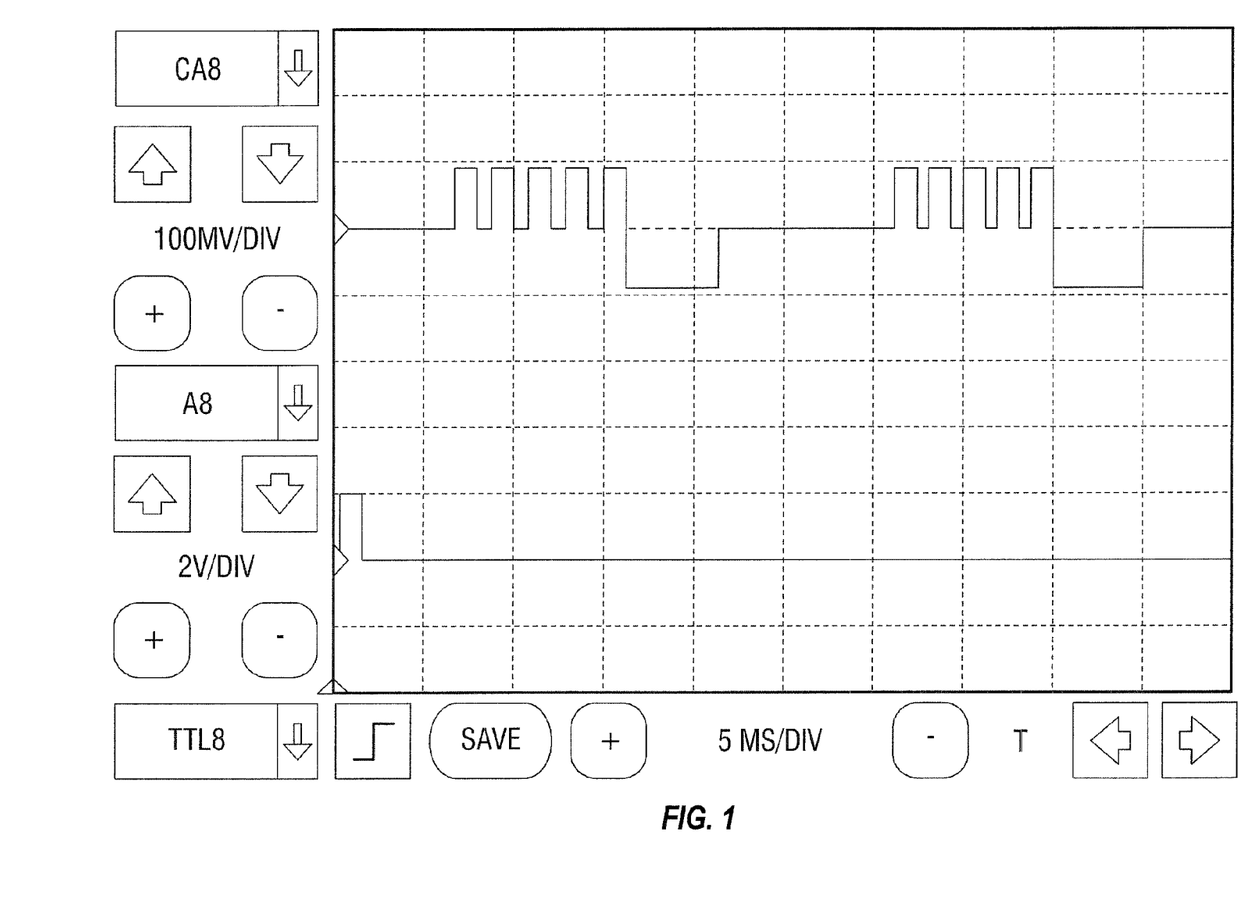
FIG. 1 illustrates an exemplary burst stimulation pattern.

All patients underwent a burst stimulation with an inter-burst interval of 40 Hz whereby each burst consisted of 5 spikes having 1 ms pulse width, 1 ms interspike interval in a charged balanced way as illustrated in FIG. 1. The burst stimuli were delivered by an 8 channel digital neurostimulator (DS8000, World Precision Instruments, Hertfordshire, England/Sarasota, Fla., USA), capable of delivering tonic and burst mode stimulation.

Figure 2:
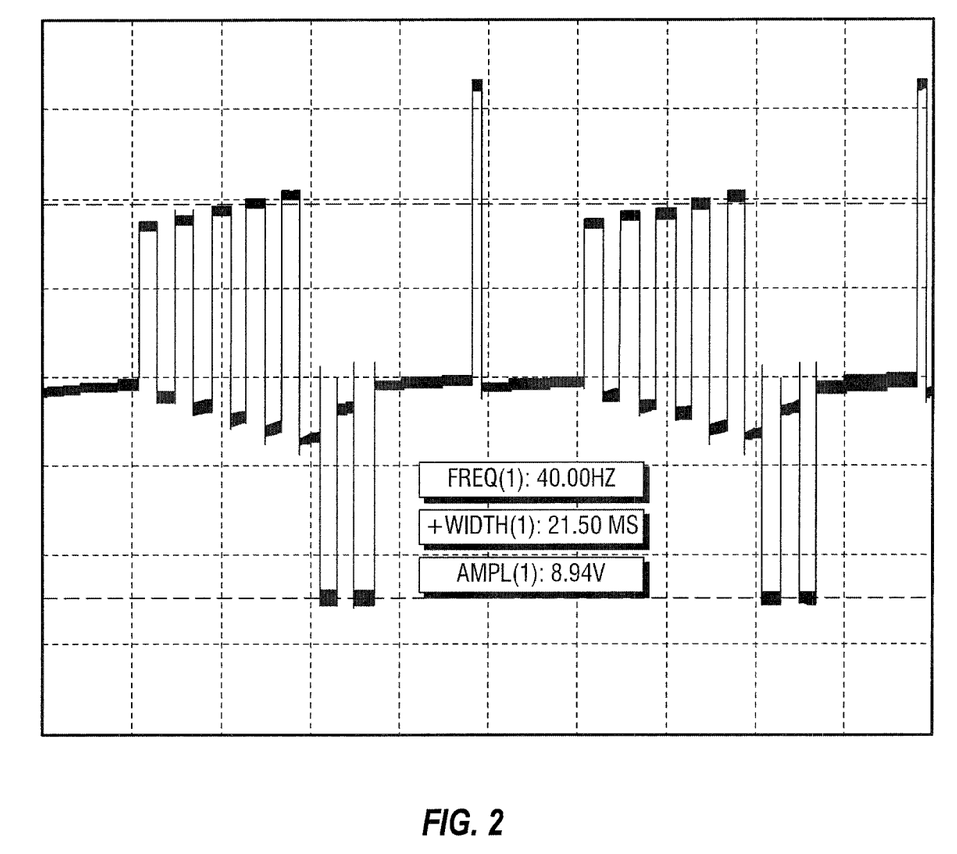
FIG. 2 illustrates an exemplary spike ramping.

If the externally delivered burst stimulation was successful in obtaining pain suppression, a commercially available internal pulse generator (IPG), capable of burst mode, was implanted (EON®, ANS Medical, Plano, Tex., USA). The IPG was programmed with similar settings, using a custom made programmer. The EON® was programmed with spike ramping (increasing amplitude of successive spikes within the burst) (FIG. 2). The ramp was added to the stimulation design to copy naturally occurring burst firing as closely as possible.

Results

None of the patients developed paresthesia during burst SCS treatment. All patients experienced reduced pain with burst SCS treatment. In some cases, pain suppression itself was not significantly better with burst stimulation than with tonic stimulation, but the absence of paresthesia was felt as a bonus to the patient. In one patient, however, pain treatment with tonic stimulation for two years prior to this study was ineffective in treating back pain, whereas treatment with burst stimulation resulted in complete pain suppression. Another patient experienced paresthesia along with pain in the absence of any stimulation, and experienced a complete suppression of both pain and paresthesia with burst SCS treatment. Furthermore, the data showed that burst stimulation treats mechanical back pain, which is often a component or complication of failed back surgery, and nociceptive pain better than tonic stimulation.

B. EXAMPLE 2

Introduction

Spinal cord stimulation is commonly used for neuropathic pain modulation. The major side effect is the onset of paresthesias. The applicant describes a new stimulation design which suppresses the pain without creating paresthesias.

Methods

Similarly, as described in Example 1, patients were implanted with dorsal column electrodes. 9 patients with neuropathic pain were implanted with paddle electrodes (Lamitrode 44, ANS Medical, Plano, Tex., USA) via a laminectomy: 3 on the cervical dorsal column at the level of C2 for cervicobrachialgia and 6 on the thoracic level at the level of T11 for lumboischialgia respectively. During the period of external stimulation the patients received the classical tonic stimulation (40 or 50 Hz) and the burst stimulation (40 Hz burst with 5 spikes at 500 Hz/burst).

Results

Figure 3A:
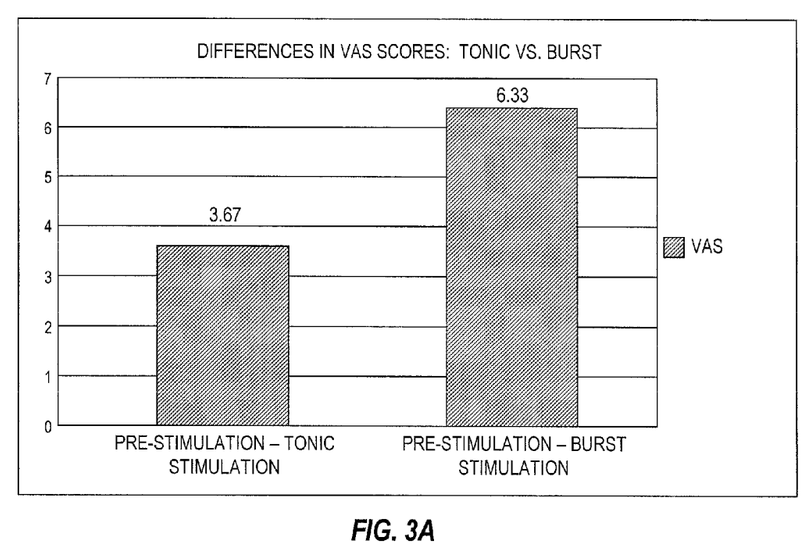
FIG. 3A shows scores from the visual analogue scale (VAS) and FIG. 3B shows scores from a McGill Shortform during pre-operative, tonic and burst stimulation.
Figure 3B:
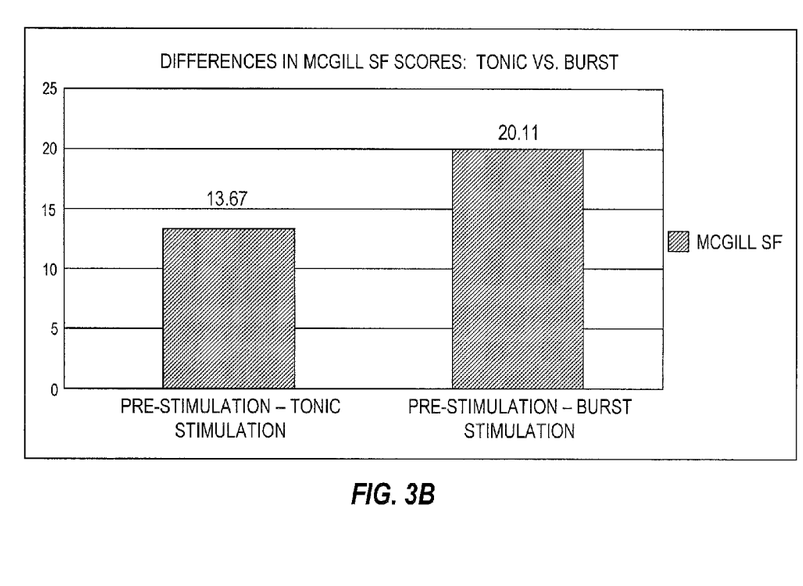

Pain scores were measured using a visual analogue scale (VAS) and a McGill Shortform during pre-operative, tonic and burst stimulation. Paresthesias were scored as present or not present. Burst stimulation was significantly better for pain suppression, both on VAS as shown in FIG. 3A (Z=2.37 p=0.018) as well as on the McGill Short form as shown in FIG. 3B (Z=1.96, p=0.050). Paresthesias were present in all 9 patients during tonic stimulation, during burst stimulation they were absent in 67% or 6 of the 9 patients. Thus, the applicant presents a new way of spinal cord stimulation using bursts in stead of tonic stimuli which suppresses neuropathic pain and does not create paresthesias.

III. Detailed Discussion of the Procedure

Figure 4:
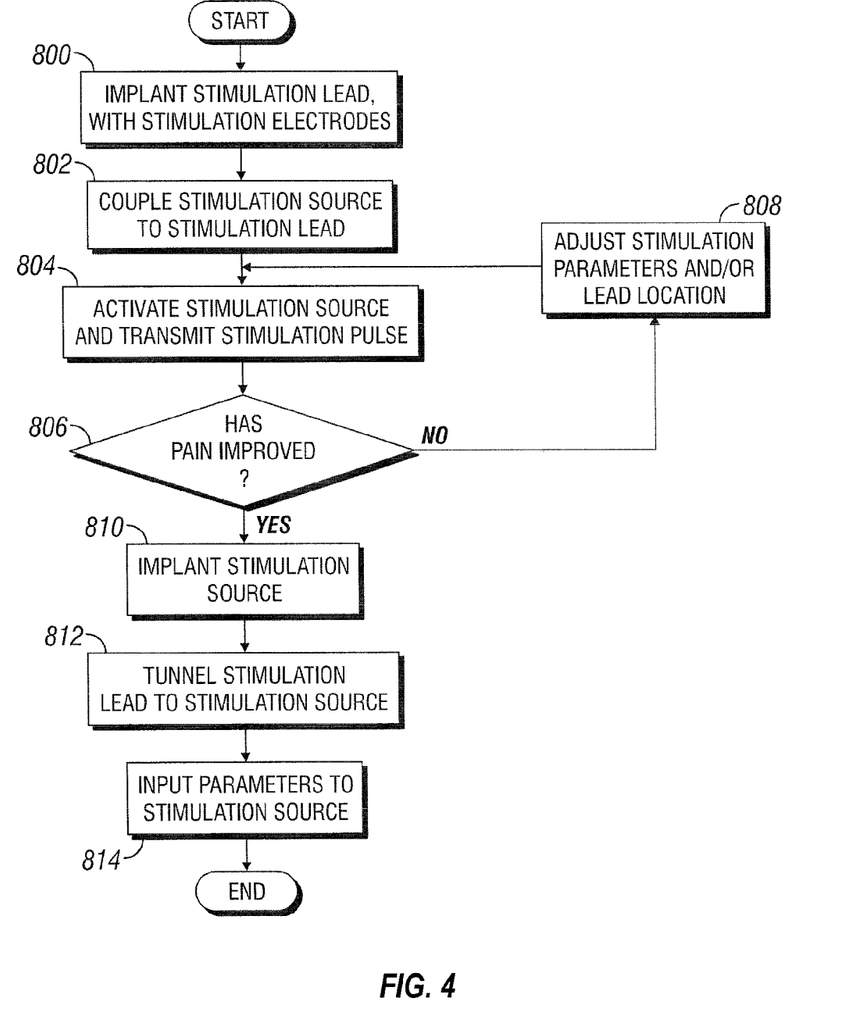
FIG. 4 is a block diagram of steps according to a method for treating pain using a spinal cord stimulation system.

The following section more generally describes FIG. 4 or an example of a procedure for pain treatment using burst SCS that optimizes the following four parameters; location for electrode placement, a set and/or range of stimulation protocols that can most completely eliminate pain and paresthesia, a set and/or range of stimulation protocols that requires the lowest voltage, and a protocol that maintains treatment efficacy over long periods of time. This treatment regimen as described herein is designed to treat a patient's pain without paresthesia.

Implantation of Simulation Lead with Stimulation Electrodes (800)

One or more stimulation leads 14 are implanted such that one or more stimulation electrodes 18 of each stimulation lead 14 are positioned in communication with the spinal cord (for the purposes described herein and as those skilled in the art will recognize, when an embedded stimulation system, such as the Bion®, is used, it is positioned similar to positioning the lead 14). Sites of interest include neuronal tissue associated with the spinal cord, for example, the spinal cord area corresponding to cervical vertebral segments C1 to C8, thoracic vertebral segments T1 to T12, or lumbar vertebral segments L1 and L2.

Techniques for implanting stimulation leads such as stimulation lead 14 are known to those skilled in the art. In certain embodiments, one or more stimulation electrodes 18 are positioned adjacent or near or in direct contact with the neuronal tissue of the spinal cord. Stimulation electrodes 18 are commonly positioned external to the dura layer surrounding the spinal cord. Stimulation on the surface of the cord is also contemplated, for example, stimulation may be applied to the spinal cord tissue as well as to the nerve root entry zone. Stimulation electrodes 18 may be positioned in various body tissues and in contact with various tissue layers; for example, subdural, subarachnoid, epidural, and subcutaneous implantation is employed in some embodiments. The electrodes are carried by two primary vehicles: percutaneous leads and a laminotomy lead.

Percutaneous leads commonly have two or more equally-spaced electrodes which are placed above the dura layer through the use of a Touhy-like needle. For insertion, the Touhy-like needle is passed through the skin between desired vertebrae to open above the dura layer. An example of an eight-electrode percutaneous lead is an OCTRODE® lead manufactured by Advanced Neuromodulation Systems, Inc. A Bion® stimulation system manufactured by Advanced Bionics Corporation is also contemplated. A percutaneous stimulation lead 14, such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (i.e., generally perpendicular to the axis of stimulation lead 14) in all directions.

Figure 6A:
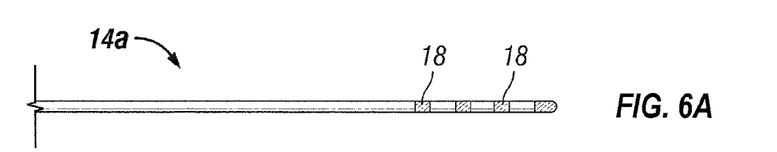
FIGS. 6A-6I illustrate example electrical stimulation leads that may be used to electrically stimulate the spinal cord.
Figure 6B:
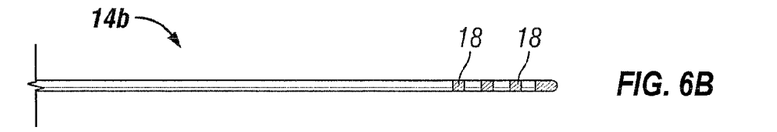
Figure 6C:
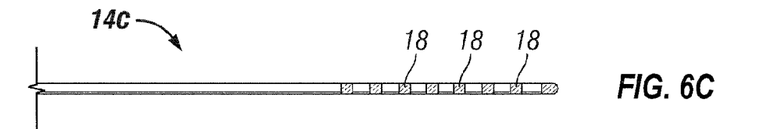
Figure 6D:
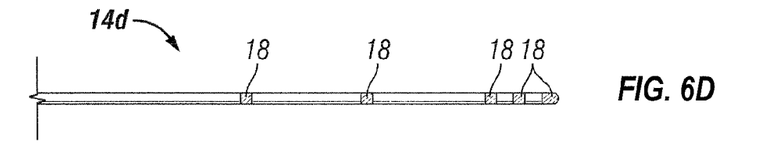
Figure 6E:
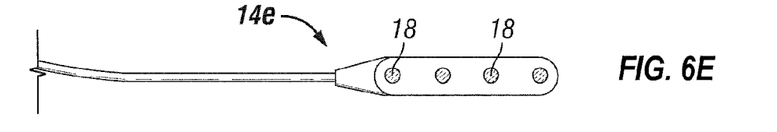
Figure 6F:
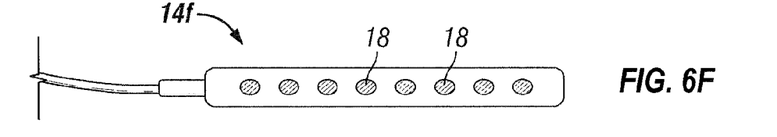
Figure 6G:
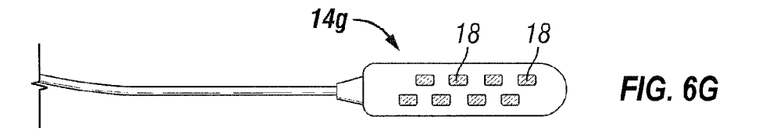
Figure 6H:
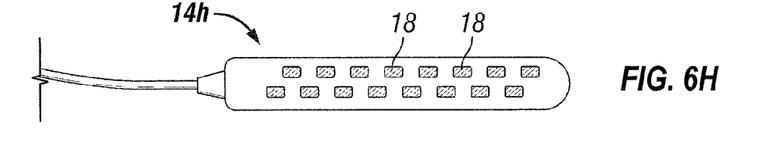
Figure 6I:
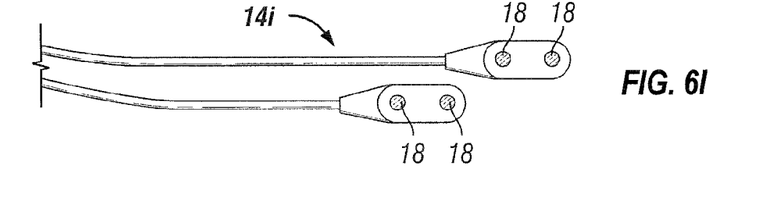
Figure 7:
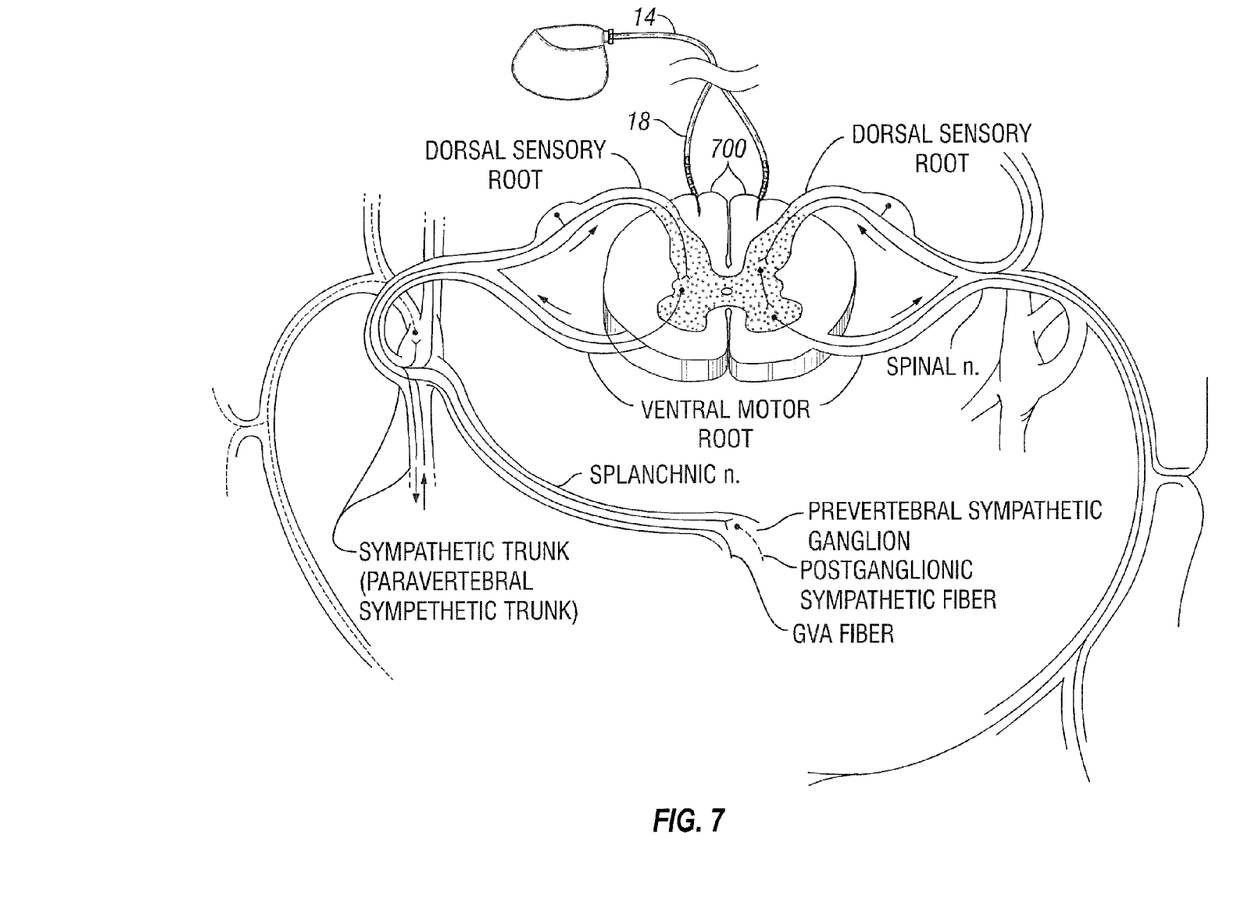
FIG. 7 illustrates an example method of implanting the stimulation system of FIGS. 5A-5B with leads in communication with the dorsal column of the spinal cord.

In contrast to the percutaneous leads, laminotomy leads have a paddle configuration and typically possess a plurality of electrodes (for example, two, four, eight, or sixteen) arranged in one or more columns. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. An example of a sixteen-electrode laminotomy lead is shown in FIG. 6H. Another example of a laminotomy lead is an eight-electrode, two column laminotomy lead called the LAMITRODE® 44, which is manufactured by Advanced Neuromodulation Systems, Inc. Implanted laminotomy leads are commonly transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place, which tends to migrate less in the operating environment of the human body. Depending on the position of insertion, however, access to the dura may only require a partial removal of the ligamentum flavum at the insertion site. In some embodiments, two or more laminotomy leads may be positioned within the epidural space, and the leads may assume any relative position to one another.

Although various types of stimulation leads 14 are shown as examples, the claimed material contemplates stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site, while bilateral electrical stimulation of the predetermined site may be accomplished using two stimulation leads 14 implanted in communication with the predetermined site on opposite sides of, for example, the spinal cord. Multi-site implantation of stimulation leads can be used.

Coupling of Stimulation Source to Stimulation Lead (802)

In general terms, stimulation system 10 includes an implantable electrical stimulation source 12 and one or more implantable electrical stimulation leads 14 for applying electrical stimulation pulses to a predetermined site. In operation, both of these primary components are implanted in a subject's body, as discussed below. In certain embodiments, stimulation source 12 is coupled directly to a connecting portion 16 of stimulation lead 14. In other embodiments, stimulation source 12 is incorporated into the stimulation lead 14 and stimulation source 12 instead is embedded within stimulation lead 14. For example, such a stimulation system 10 may be a Bion® stimulation system manufactured by Advanced Bionics Corporation. Whether stimulation source 12 is coupled directly to or embedded within the stimulation lead 14, stimulation source 12 controls the stimulation pulses transmitted to one or more stimulation electrodes 18 located on a stimulating portion 20 of stimulation lead 14, positioned in communication with a predetermined site, according to suitable stimulation parameters (e.g., duration, amplitude or intensity, frequency, pulse width, etc.). The predetermined site is the spinal cord in this example and may be the dorsal column of the spinal cord in a preferred embodiment.

Figure 5A:
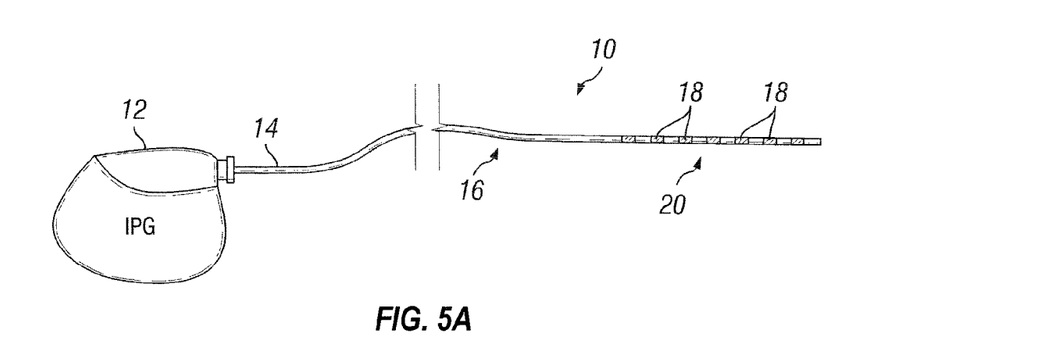
FIGS. 5A-5B illustrate example stimulation systems for electrically stimulating the spinal cord.
Figure 5B:
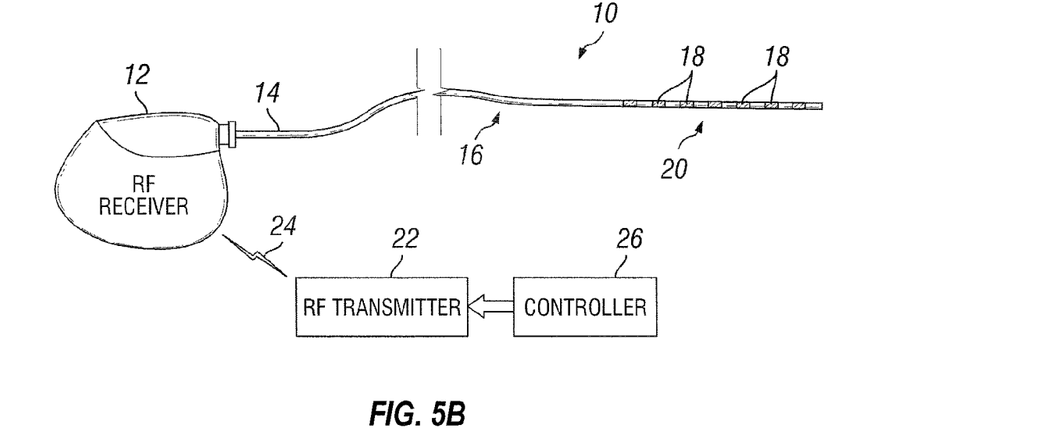

In one embodiment, as shown in FIG. 5A, stimulation source 12 includes an implantable pulse generator (IPG). In another embodiment, as shown in FIG. 5B, stimulation source 12 is capable of wireless communications and, preferably, is capable of being recharged using inductive coupling with an external charging device. An example of such a stimulation source is the Eon® System available from Advanced Neuromodulation Systems, Inc. In another embodiment, the IPG can be optimized for high frequency operation as described in U.S. Published Application No. US20060259098, which is incorporated herein by reference. After implantation, the stimulation source 12 receives wireless signals from a wireless transmitter 22 located external to the person's body. The wireless signals are represented in FIG. 5B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the implanted pulse generator 12, and pulse generator 12 uses the control signals to vary the stimulation parameters of stimulation pulses transmitted through stimulation lead 14 to the predetermined spinal column site. Wireless transmitter 22 and controller 26 can be integrated within a single device and are commercially distributed with implantable pulse generator products.

Activate Stimulation Source and Transmit Trial Stimulation Pulse (804)

Conventional neuromodulation devices can be modified to apply burst stimulation to nerve tissue of a patient by modifying the software instructions and/or stimulation parameters stored in the devices. Specifically, conventional neuromodulation devices typically include a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device and accompanying stimulation parameters. An example of a commercially available neuromodulation device that can be modified or programmed to apply burst stimulation includes the EON®, manufactured by Advanced Neuromodulation Systems, Inc.

These conventional neuromodulation devices can be adapted by programming the microprocessor to deliver a number of spikes (relatively short pulse width pulses) that are separated by an appropriate inter-spike interval. Thereafter, the programming of the microprocessor causes the pulse generation module to cease pulse generation operations for an inter-burst interval. The programming of the microprocessor also causes a repetition of the spike generation and cessation of operations for a predetermined number of times. After the predetermined numbers of repetitions have been completed, the microprocessor can cause burst stimulation to cease for an amount of time and resume thereafter.

Also, in some embodiments, the microprocessor could be programmed to cause the pulse generation module to deliver a hyperpolarizing pulse before the first spike of each group of multiple spikes. The microprocessor can be programmed to allow the various characteristics of the burst stimulus to be set by a physician to allow the burst stimulus to be optimized to treat the patient's pain. For example, the spike amplitude, the inter-spike interval, the inter-burst interval, the number of bursts to be repeated in succession, the amplitude of the various pulses, and other such characteristics could be controlled using respective parameters accessed by the microprocessor during burst stimulus operations. These parameters could be set to desired values by an external programming device via wireless communication with the implantable neuromodulation device.

In another embodiment, a neuromodulation device can be implemented to apply burst stimulation using a digital signal processor and one or several digital-to-analog converters. The burst stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst parameters. A doctor, the patient, or another user of stimulation source 12 may directly or indirectly input stimulation parameters to specify or modify the nature of the stimulation provided.

Examples of burst stimulation are found in U.S. Published Application No. US20060095088, and incorporated herein by reference in its entirety. The burst stimulation may generate bursts of a plurality of electrical pulses with an inter-burst frequency in the range of about 1 Hz to about 100 Hz, more particular, in the range of about 1 Hz to about 50 Hz, and more particularly, about 40 Hz. The inter-burst interval has a duration in the range of about 1 milliseconds to about 5 seconds, more preferably, about 10 milliseconds to about 300 milliseconds. The inter-burst interval need not be constant and can be varied in a programmable manner or varied pseudo-randomly by the pulse generator (e.g., random or irregular harmonics).

In one embodiment the initial stimulation protocol in step 804 will be a non-saturating stimulation protocol that only partially eliminates pain sensation and/or paresthesia. For example, a non-saturating protocol may be created by employing voltages or stimulation protocols known not to be completely effective in eliminating pain and/or paresthesia. In some embodiments the initial stimulation protocol in step 804 may involve tonic mode or burst mode stimulations. Using such non-saturating protocols, a location of maximum efficacy may be ascertained, with regards to the location of stimulation lead 14 and/or the differential activation of various stimulation electrodes 18. In other embodiments, a burst stimulation protocol may be designed for the patient at step 804 wherein a voltage is applied that only partially eliminates pain sensation and/or paresthesia, and various burst mode stimulation parameters are tested in order to determine a protocol of maximum efficacy. Once an optimal location and protocol have been determined, the voltage may be adjusted to completely eliminate sensation of pain and paresthesia. In other embodiments, subsequent to location selection, step 804 may include the application of a saturating stimulation protocol that reduces pain and paresthesia as completely as possible.

Assessment of Pain (806)

Those skilled in the art recognize that there are many methods to assess and quantify the patient's experience of pain. One example of a method for pain measurement is the use of the Visual Analog Scale (VAS). In the VAS patients are asked to rank their pain by making a mark on a bar that is labeled "no pain" on one end, and "pain as bad as possible" on the other end. Patients may mark the bar anywhere between the two opposite poles of perceived pain sensation. This mark can then be given any quantitative value such as fractional, decimal, or integer values by the clinician and used as a semi-quantitative pain measurement. Another pain measurement scale is the McGill Pain Questionnaire (SF-MPQ) that provides the patient with descriptors and the patient to rates the severity or intensity of the pain on a scale of 0=none, 1=mild, 2=moderate, or 3 severe. Other various tests for pain severity can also be used in which patients may rank their pain on a scale between zero and ten, by a scale of faces depicting various emotions from happy to very sad and upset, and by answering a variety of questions describing the pain. In preferred embodiments, the patient's pain is assessed prior to and during the trial implantation procedure, for example prior to process 800, and then again at process 806. In other embodiments, informal subjective questioning of the person, and/or formal subjective testing and analysis may be performed to determine whether the subject's pain has sufficiently improved throughout the intra-implantation trial stimulation.

In some embodiments, it is considered that several cycles of intra-implantation trials may be required. A comparison of the patient's perceived pain between multiple cycles of intra-implantation trial stimulation will be used to determine the optimal location and stimulation protocol. In further embodiments, steps 804 through 808 represent a repetitive cycle that ends when an optimal location and protocol have been selected. In some embodiments, once the stimulation lead 14 has been properly positioned such that subject's perception of pain is improved or absent, intra-implantation stimulation may be considered complete. It is contemplated that stimulation parameters may be modified to maximize the effectiveness of the therapy both prior to and subsequent to the end of the intra-implantation trial stimulations.

In addition to utilizing pain scores and grading and objective measures including use of additional pain medications (e.g., reduction in the amount of medication consume or elimination of the consumption of pain medications), other methods to determine improvement of a patient's pain may comprise administering various standardized questionnaires or tests to determine the patient's neuropsychological state. It is well known by those in the art that depression is the most common emotional disturbance in patients with chronic pain. Such neuropsychological testing can include, but are not limited to (i.e., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, or N-BAC).

Adjustment of Stimulation Parameters and/or Lead Location (808)

If the subject's pain has not sufficiently improved at process 806, or if the reduction of pain and paresthesia is determined to be incomplete or inadequate during the intra-implantation trial stimulation procedure, stimulation lead 14 may be moved incrementally or even re-implanted, one or more stimulation parameters may be adjusted, or both of these modifications may be made at process 808 and the trial stimulation and analysis repeated until the pain has sufficiently improved without paresthesia. In other embodiments, adjustments may be made at process 808 even when complete reduction of pain and paresthesia is noted. For example, further refinement of electrode location may be desired.

Implantation of Stimulation Source (810)

In some embodiments the intra-trial stimulation period is determined to be complete during process 806. In other embodiments, the intra-implantation trial stimulation is not performed, and the method proceeds from process 802 to 810. Once the location for the stimulation lead 14 has been determined, the stimulation lead may be properly implanted and secured and a stimulation source 12 may be surgically implanted at process 810. Techniques for implanting stimulation sources such as stimulation source 12 are known to those skilled in the art. For non-embedded systems, the implant site is typically a subcutaneous pocket formed to receive and house stimulation source 12. The implant site is usually located some distance away from the insertion site, such as in or near the lower back or buttocks.

Tunneling of Stimulation Lead to Stimulation Source (812)

Where stimulation lead 14 includes connecting portion 16, connecting portion 16 may be tunneled, at least in part, subcutaneously to the implant site of stimulation source 12 at step 812. Some embodiments may use a non-implantable stimulation source.

Input of Parameters to Stimulation Source (814)

During process 814, a doctor, the patient, or another user of stimulation source 12 may directly or indirectly input stimulation parameters for controlling the nature of the electrical stimulation provided to the target spinal tissue area, if not already set during any intra-implantation trial stimulation period. Where appropriate, post-implantation trial stimulation may be conducted to determine the efficacy of various types of burst stimulation. Examples of efficacy metrics may include the minimum required voltage for a given protocol to achieve maximum and/or complete reduction of pain and or paresthesia. Efficacy metrics may also include a measurement of the presence and/or degree of habituation to a given protocol over one or more weeks or months, and any necessary modifications made accordingly. Such assessments can be conducted by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems. Furthermore, pain assessment as described above may be preformed to determine the efficiency of the protocol and based upon the assessment the stimulation parameters may be optimized or modified to achieve more efficient pain control.

In certain embodiments, it may be desirable for the patient to control the therapy to optimize the operating parameters to achieve increased or optimized pain management or treatment. For example, the patient can alter the pulse frequency, pulse amplitude and pulse width using a hand held radio frequency device that communicates with the IPG. Once the operating parameters have been altered by the patient, the parameters can be stored in a memory device to be retrieved by either the patient or the clinician. Yet further, particular parameter settings and changes therein may be correlated with particular times and days to form a patient therapy profile that can be stored in a memory device.

Although example steps are illustrated and described, the claimed material contemplates two or more steps taking place substantially simultaneously or in a different order. In addition, the claimed material contemplates using methods with additional steps, fewer steps, or different steps, so long as the steps remain appropriate for implanting stimulation system 10 into a person for electrical stimulation of the a predetermined site, such as, for example the dorsal column at the cervical area to treat pain without paresthesia. In some embodiments the level of the spinal cord in which the stimulation is to occur consists of segments T8-T11. In other embodiments the level of the spinal cord in which the stimulation is to occur consists of segments C2 or C3.

IV. Types of Pain to be Treated

Burst firing is a more effective treatment for many neurological conditions as shown in this application as well as U.S. Published Application No. 20060095088. It is also known to one skilled in the art that burst stimulation is a more powerful activator of inhibition than tonic stimulation (Kim and McCormick, 1998).

Mechanistically, it is known that nociceptive neurons in the dorsal column fire in burst mode (Lopez-Garcia et al., 1994). Lamina I and II receive predominantly nociceptive input (Ruscheweyh and Sandkuhler, 2002). Most burst firing is noted in lamina II (Ruscheweyh and Sandkuhler, 2002). Projection neurons in lamina I that fire in burst mode (Ruscheweyh et al., 2004) receive afferent C-fibers. It is known that a good correlation exists between the reported pain sensation and the activity evoked in the afferent C-fibers (Olausson, 1998). Thus, it is envisioned that the burst type therapeutic stimulation system described herein will more efficient and effective at treating pain compared to typical tonic type SCS protocols.

Pain of a moderate or high intensity is typically accompanied by anxiety. Thus, one of skill in the art is cognizant that pain may have dual properties, for example sensation and emotion. Chronic pain can be associated with several factors that include, but are not limited to lassitude, sleep disturbance, decreased appetite, loss of taste for food, weight loss, diminished libido, constipation, or depression. Thus, in certain embodiments, in connection with improvement the electrical stimulation may have a "brightening" effect on the person such that the person looks better, feels better, moves better, thinks better, eats better, sleeps better, and otherwise experiences an overall improvement in quality of life.

In some embodiments, therapeutic stimulation system may be used to treat acute pain. Acute pain is transient in nature and generally considered by those skilled in the art to be an important adaptive feature of animal survival. It is usually associated with an immediate injurious process such as soft tissue damage, infection, or inflammation and serves the purpose of notifying the animal of the injurious condition, thus allowing for treatment or preventing further injury. In most cases of acute pain, adequate treatment may be obtained through the administration of analgesic drugs. In some circumstances however, treatment of acute pain by drug delivery is either sub-optimal due to potential side-effects, or not possible. Examples include patients with histories of drug abuse, contraindications with other necessary drugs, allergies or liver problems, and women in childbirth.

A common method for pain treatment during childbirth is the use of epidural administration of drugs via injection or catheterization. The administration of anaesthetic or analgesic drugs via epidural has many drawbacks. In addition to all of the potential negative side effects the drug may have on the mother, there are potential complications for the chilbirth and early childhood development as well. For example the use of epidurals has been negatively correlated with vaginal birth outcomes in humans (Roberts et al., 2000). It has also been found that use of epidurals is positively correlated with an early abandonment of breastfeeding in human infants (Torvaldsen et al., 2006). Additionally many women find the analgesic effects of epidurals insufficient to treat their pain both during and after childbirth. Because of the nonspecific effects of the drugs commonly used, high dosages will cause non-specific numbness and muscular weakness, which can interfere with the normal birthing process. Burst SCS during childbirth may prove effective in alleviating pain completely without causing side effects such as muscular weakness in the mother, and without adversely affecting the child during or after childbirth.

In some embodiments, the therapeutic stimulation system may be used to treat chronic pain. As many as one in five people in the world currently suffer from chronic pain. Some forms of chronic pain are obviously associated with a chronic injury condition that may or may not be treatable. Other forms of chronic pain such as neuropathic and phantom pain may not be obviously associated with a continuing tissue injury and are discussed in greater detail below. All of the different forms of chronic pain are similar in that they at least involve activation of nociceptive fibers in the peripheral nervous system and subsequently, nociceptive central fibers in the dorsal spinal cord. All forms of chronic pain are also similar in that they provide little value to the person experiencing them, and may substantially reduce that person's quality of life.

It is known to one skilled in the art that administration of analgesic drugs in the treatment of chronic pain is almost always non-optimal. There are several reasons for this. First of all, most drugs used in the treatment of pain become less effective in treating pain over long periods of time such as in chronic pain conditions. Secondly, many drugs that treat pain are addictive to the patient, and may result in substance abuse and or withdrawal symptoms by the patient subsequent to treatment. Thirdly, many drugs used to treat pain produce unwanted side effects that are increased during long term use. Such side effects can include toxic effects on the patient's body such as the nervous system itself and other internal organs such as the heart, liver, and kidneys. Overdoses of many analgesic drugs can be fatal.

In some embodiments, the therapeutic stimulation system may be used to treat neuropathic pain. Neuropathic pain is pain that results from damage to the nervous system itself. It may exist independently of any other form of tissue injury outside of the nervous system. It can be caused by myriad factors such as disease (HIV, Herpes, Diabetes, Cancer, autoimmune disorders), acute trauma (surgery, injury, electric shock), or chronic trauma (repetitive motion disorders, chemical toxicity such as alcohol, chemotherapy, or heavy metals). Neuropathies can originate anywhere in the central or peripheral nervous system, but only in some cases does this produce neuropathic pain. One notable feature of neuropathic pain is that it often involves a combined pain sensation. The sensation is often described as burning, shocking, or tingling pain. It is theorized that these unique pain sensations are due to the combined activation of both nociceptive and non-nociceptive sensory pathways from the same region of the body. According to the previously described tenets of Gate Control Theory, nociceptive and non-nociceptive fibers from a given dermatome normally mutually inhibit one another upon activation and therefore the two subsequent sensations should rarely if ever co-exist temporally in the brain. Thus, neuropathies often produce disturbing and confusing pain sensations that are quite unlike other common forms of pain.

In some embodiments, the therapeutic stimulation system may be used to treat phantom pain. Phantom pain is a condition whereby the patient senses pain in a part of the body that is either no longer physically present due to amputation, or is known to be completely insensate due to total peripheral nerve destruction. When severe damage occurs in peripheral tissue such that nociceptive nerve endings are destroyed, but the nociceptive neuron itself is not severed from the spinal cord, phantom pain may develop. In phantom pain, the tonic firing rate of the nociceptive sensory neurons increases (Yamashiro et al., 2003), as does the amount of burst firing in the deafferented receptive fields (Rinaldi et al., 1991; Jeanmonod et al., 1996; Radhakrishnan et al., 1999) in the somatosensory thalamic nuclei (Rinaldi et al., 1991; Lenz et al., 1998), as well as activity in the in the intralaminar nuclei (Weigel and Krauss 2004). Synchrony in firing is also increased. This is similar to what is seen in animal neuropathic pain models (Lombard and Besson 1989; Nakamura and Atsuta 2004) (Yamashiro et al., 1991). These results suggest that in phantom pain, decreased spike frequency adaptation and increased excitability develops after injury to sensory neurons. Through decreased $Ca^{2+}$ influx, the cell becomes less stable and more likely to initiate or transmit bursts of action potentials (McCallum et al., 2003).

In some embodiments, the therapeutic stimulation system may be used to treat hyperalgesia and or allodynia. Hyperalgesia is an increased sensitivity to nociceptive or painful stimuli that occurs subsequent to tissue injury or nociceptive pathway activation. Allodynia is very similar to hyperalgesia and describes a condition whereby normally non-noxious stimuli are perceived as painful. Both hyperalgesia and allodynia can be divided into primary and secondary categories or conditions.

Primary hyperalgesia and allodynia is an increase in sensitivity to painful and previously non-painful stimuli in a region of the body that has undergone tissue injury. Primary hyperalgesia is due in part to changes in the spinal cord that are mediated by the input from primary afferent C-fiber nociceptors (Ikeda et al., 2006). Signals from higher brain regions are also sent to the spinal cord that can decrease primary hyperalgesia (Vanegas, 2004). As such primary hyperalgesia may be treatable by burst SCS.

Secondary hyperalgesia is an increase in pain sensitivity globally and requires descending input into the periphery from various pain processing centers in the brain. Pain processing centers in the brain normally require an initial nociceptive stimulus from the periphery in order to induce hyperalgesia. Moreover, all secondary hyperalgesia signals must pass back through the spine to sensitize the peripheral nociceptors and thus induce the hyperalgesia. Therefore, any therapy that blocks the nociceptive signal at the level of the spinal cord may be either block secondary hyperalgesia in the first place in acute pain treatments, or terminate hyperalgesia upon continuous treatment of chronic pain. Since burst stimulation is a more powerful activator of inhibition than tonic stimulation, it may suppress this burst firing nociceptive pathway, whereas tonic stimulation may not.

REFERENCES

All patents and publications mentioned in the specification are indicative of the levels of those skilled in the art to which the claimed material pertains. All patents and publications are herein incorporated by reference to the same extent as if each individual publication was specifically and individually indicated to be incorporated by reference.

Chadron et al., J Comput Neurosci 2004; 17(2):127-36.
Huang et al., Neuron 2005; 45(2):201-6.
Hunt et al., 1975 Surg Neurol 4:153-156.
Jeanmonod et al., Brain 1996; 119 (Pt 2):363-75.
Kumar et al., Surg Neurol 1996; 46:363-369.
Lenz et al., Neuroscience 1998; 86(4):1065-81.
Lisman, Trends Neurosci 1997; 20(1):38-43.
Lombard & Besson, Brain Res 1989; 477(1-2):48-56.
Moller, Neural plasticity and disorders of the nervous system. (in press) ed. Cambridge: Cambridge University Press, 2006.
Nakamura & Atsuta, J Orthop Sci 2004; 9(4):386-91.
Oswald et al., J Neurosci 2004; 24(18):4351-62.
Radhakrishnan et al., Pain 1999; 80(3):567-75.
Rinaldi et al., J Neurosurg 1991; 74(3):415-21.
Sherman, Nat Neurosci 2001; 4(4):344-6.
Sherman, Trends Neurosci 2001; 24(2):122-6.
Swadlow & Gusev, Nat Neurosci 2001; 4(4):402-8.
Weigel et al., Stereotact Funct Neurosurg 2004; 82(2):115-126.
Yamashiro et al., Acta Neurochir Suppl (Wien) 1991; 52:130-2.
Yamashiro et al., Acta Neurochir Suppl 2003; 87:153-5.
Huskisson E C. J Rheumatol 1982; 9:768-769
Roberts et al., British Medical Journal (BMJ), v 321:p 137, 15 Jul. 2000
Torvaldsen et al., Int Breastfeed J. 2006 Dec. 11; 1:24.
Ikeda et al., Science. 2006 Jun. 16; 312(5780):1659-62.
Vanegas H. Neurosci Lett. 2004 May 6; 361(1-3):225-8. Review.

Although the claimed material and its advantages have been described in detail, it should be understood that various changes, substitutions and alterations can be made herein without departing from the claimed material as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of treating chronic pain, including lower back pain and leg pain, in a patient with spinal cord stimulation, the method comprising:

storing one or more operating parameters for a high frequency stimulus having a plurality of pulses, wherein the high frequency stimulus comprises at least respective pairs of pulses that have a pulse separation within a range of 0.1 milliseconds to 1.0 milliseconds;

operating a pulse generator to generate electrical pulses of the high frequency stimulus; and applying the generated electrical pulses of the high frequency stimulus to the patient through a set of one or more electrodes of an electrical lead implanted within epidural space of the patient to treat the lower back pain and leg pain of the patient without causing paresthesia in the lower back or legs of the patient where resulting pain relief occurs during application of the pulses of the high frequency stimulus.

2. The method of claim 1 wherein the applying treats chronic pain resulting from failed back surgery syndrome.

3. The method of claim 1 further comprising:
pseudo-randomly varying a pulse repetition frequency for the pulses within the high frequency stimulus.

4. The method of claim 1 further comprising:
applying one or more quiescent intervals within the high frequency stimulus.

5. The method of claim 4 wherein each quiescent interval is between approximately 10 milliseconds to 300 milliseconds.

6. The method of claim 1 wherein an amplitude of pulses within a plurality of groups of pulses within the high frequency stimulus increases within each respective group.

7. The method of claim 6 wherein each group within the plurality of group of pulses is terminated by a charge balancing pulse that has a pulse width greater than a pulse width employed for other pulses of the respective group.

8. The method of claim 1 wherein the set of electrodes are disposed within at least one vertebral level selected from the listing consisting of: T8, T9, T10, T11, and T12.

9. A method of treating chronic pain in a patient with spinal cord stimulation, the method comprising:
storing one or more operating parameters for a burst stimulus having a plurality of groups of pulses, wherein (i) the burst stimulus is substantially quiescent between each group of the plurality of groups of pulses with a quiescent interval of at least 1 millisecond and less than about 5 seconds and (ii) the burst stimulus comprises respective groups of pulses with at least one pulse that is followed by another pulse within 0.1 to 10.0 milliseconds;
operating a pulse generator to generate electrical pulses of the burst stimulus; and
applying the burst stimulus to the patient through one or more electrodes of an electrical lead implanted within epidural space of the patient to treat the chronic pain of the patient without causing paresthesia in the patient.

10. The method of claim 9 wherein the applying treats pain resulting from failed back surgery syndrome.

11. The method of claim 9 further comprising:
pseudo-randomly varying a pulse repetition frequency for the plurality of groups of pulses within the burst stimulus.

12. The method of claim 9 further comprising:
pseudo-randomly varying the quiescent interval for the plurality of groups of pulses within the burst stimulus.

13. The method of claim 9 wherein the quiescent interval is between approximately 10 milliseconds to 300 milliseconds.

14. The method of claim 9 wherein an amplitude of pulses within the plurality of groups of pulses increases within each respective group.

15. The method of claim 9 wherein each group within the plurality of group of pulses is terminated by a charge balancing pulse that has a pulse width greater than a pulse width employed for other pulses of the respective group.

16. The method of claim 9 wherein the groups of pulses within the burst stimulus repeat at approximately 40 Hz.

17. The method of claim 9 wherein the epidural space of the patient is further defined as thoracic epidural space of T8, T9, T10, T11, T12 or a combination thereof.

\* \* \* \* \*